US012721896B1

(12) United States Patent
Kinion et al.

(10) Patent No.: US 12,721,896 B1
(45) **Date of Patent: *Sep. 1, 2026**

(54) COMPOSITIONS AND METHODS FOR SUPPRESSING INTRACELLULAR SYNTHESIS OF THE BETA SUBUNIT OF HUMAN CHORIONIC GONADOTROPIN

(71) Applicant: James Summerton Living Trust dated May 15, 2008, Corvallis, OR (US)

(72) Inventors: Janet Helena Kinion, Corvallis, OR (US); James E. Summerton, Corvallis, OR (US)

(73) Assignee: James Summerton, Corvallis, OR (US), Living Trust dated May 15, 2008

( * ) Notice: Subject to any disclaimer, the term of this patent is extended or adjusted under 35 U.S.C. 154(b) by 0 days.

This patent is subject to a terminal disclaimer.

(21) Appl. No.: 19/533,261

(22) Filed: Feb. 8, 2026

Related U.S. Application Data

(63) Continuation-in-part of application No. 19/058,559, filed on Feb. 20, 2025, now Pat. No. 12,590,308.

(51) Int. Cl.

| | |
|---|---|
| ***C12N 15/113*** | (2010.01) |
| ***A61K 9/00*** | (2006.01) |
| ***A61K 38/00*** | (2006.01) |
| ***A61K 45/06*** | (2006.01) |
| ***C12Q 1/6886*** | (2018.01) |

(52) U.S. Cl.
CPC ........... *A61K 45/06* (2013.01); *A61K 9/0019* (2013.01); *A61K 38/00* (2013.01); *C12N 15/113* (2013.01); *C12Q 1/6886* (2013.01); *C12N 2310/3233* (2013.01)

(58) Field of Classification Search
CPC ...................... C12N 15/113; C12N 2310/3233
See application file for complete search history.

(56) References Cited

U.S. PATENT DOCUMENTS 12,590,308 B1 * 3/2026 Kinion .............. C12N 15/1136

* cited by examiner

*Primary Examiner* — J. E. Angell
(74) *Attorney, Agent, or Firm* — David S. Alavi

(57) ABSTRACT

A composition of matter includes an antisense phosphorodiamidate morpholino oligomer (MO) that includes an MO base sequence. The MO base sequence includes at least the base sequence gcagcccctggaacat (SEQ ID NO: 8) and is arranged to bind a corresponding complementary base sequence of messenger RNA (mRNA) transcribed from one or more genes for the beta subunit of human chorionic gonadotropin (hCG-β). An inventive method, for suppressing intracellular synthesis of a beta subunit of human chorionic gonadotropin (hCG-β), includes introducing such an MO into one or more cells.

20 Claims, 8 Drawing Sheets

Specification includes a Sequence Listing.

| | |
|---|---|
| SEQ ID NO: 1 | gcagcagcccctggaacatctccatc |
| SEQ ID NO: 2 | cagcagcccctggaacatctccatc |
| SEQ ID NO: 3 | gcagcccctggaacatctccatcct |
| SEQ ID NO: 4 | cagcagcagcccctggaacatctcc |
| SEQ ID NO: 5 | gcaacagcagcagcccctggaacat |
| SEQ ID NO: 6 | cagcagcagcccctggaacatctccatc |
| SEQ ID NO: 7 | caacagcagcagcccctggaacatctcc |
| SEQ ID NO: 8 | gcagcccctggaacat |

COMPOSITIONS AND METHODS FOR SUPPRESSING INTRACELLULAR SYNTHESIS OF THE BETA SUBUNIT OF HUMAN CHORIONIC GONADOTROPIN

CROSS-REFERENCE TO RELATED APPLICATIONS

This application is a continuation-in-part of U.S. non-provisional application Ser. No. 19/058,559 entitled "Compositions and methods for suppressing intracellular synthesis of the beta subunit of human chorionic gonadotropin" filed Feb. 20, 2025 in the names of Kinion et al, said application being incorporated herein by reference in its entirety.

SEQUENCE LISTING

This application includes a sequence listing which has been submitted electronically in XML format. The XML file containing the sequence listing is named MOTH02CP1_sequence_listing.xml, was created on 22 Jan. 2026, and is 11,288 bytes in size. The sequence listing is being submitted via the Office electronic filing system concurrently with filing of the instant application and is hereby incorporated by reference into the specification in its entirety.

TECHNICAL FIELD

The technical field relates to antisense phosphorodiamidate morpholino oligomers (MOs). In particular, novel MOs, and methods for their use, are disclosed that bind certain complementary base sequences of messenger RNA (mRNA) transcribed from one or more genes for the beta subunit of human chorionic gonadotropin (hCG-β).

BACKGROUND

Human chorionic gonadotropin (hCG) is a normally occurring glycoprotein hormone and consists of an alpha subunit (hCG-α) and a beta subunit (hCG-β). hCG is normally produced during pregnancy by expression of the corresponding genes; at other times those genes are normally not expressed, and hCG is not normally detectable in a non-pregnant human body.

It has been observed that many human cancers include inappropriate expression of the genes for hCG, and the resulting hormone plays a role in the development, growth, and invasiveness of those cancers. Various attempts have been made to suppress the formation or activity of hCG as a form of cancer therapy, thus far with little or only limited success. Previous approaches have included, e.g., vaccination to trigger development of hCG-specific antibodies, administration of hCG-specific monoclonal antibodies, or using a C-terminal peptide (CTP) to target the CTP domain of the beta subunit of hCG.

SUMMARY

An inventive composition of matter comprises an antisense phosphorodiamidate morpholino oligomer (MO) that includes an MO base sequence. The MO base sequence includes at least the base sequence gcagcccctggaacat (SEQ ID NO: 8) and is arranged to bind a corresponding complementary base sequence of messenger RNA (mRNA) transcribed from one or more genes for the beta subunit of human chorionic gonadotropin (hCG-3). An inventive method, for suppressing intracellular synthesis of a beta subunit of human chorionic gonadotropin (hCG-β), includes introducing such an MO into one or more cells.

In some examples the one or more genes can include one or more or all of the CGB3, CGB5, CGB7, or CGB8 genes. In some examples the MO base sequence can comprise one of the base sequences in the table of FIG. 3 and in the incorporated sequence listing. In some examples the composition can include a delivery moiety, linked to (covalently or otherwise), including, or containing the MO, that is structurally arranged for attaching to a membrane of a cell and enabling the MO to enter the cell.

In some examples the cells into which the MO is introduced are cancer cells. In some examples the MO is introduced into the cancer cells in vitro; in some other examples the MO is introduced into the cancer cells in vivo. In some examples, suppressing expression of one or more hCG-β genes suppresses cell division of the cancer cells, or results in cell death of 50% or more of the cancer cells.

Objects and advantages pertaining to suppression of intracellular synthesis of hCG-β may become apparent upon referring to the example embodiments illustrated in the drawings and disclosed in the following written description or appended claims.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

FIG. 2 is a table showing base sequences and their corresponding sequence ID numbers; the base sequences shown in the table of FIG. 2 are also included in the appended sequence listing (MOTH02CP1_sequence_listing.xml).

FIG. 4A shows the structure of a generic MO covalently linked (as in FIG. 3B, with a specific example of a linker) to a specific example of a cationic dendrimer. FIG. 4C shows the structure of a generic MO covalently linked (as in FIG. 3C, with a second example of a cleavable linker) to a specific example of a cationic dendrimer. The cationic dendrimers are shown in their un-ionized forms; under physiological conditions (e.g., within a cell or in body fluids) the end groups of the dendrimer would be protonated and therefore positively charged.

The embodiments depicted are shown only schematically; all features may not be shown in full detail or in proper proportion; for clarity certain features or structures may be exaggerated or diminished relative to others or omitted entirely; the drawings should not be regarded as being to scale unless explicitly indicated as being to scale. The embodiments shown are only examples and should not be construed as limiting the scope of the present disclosure or appended claims.

DETAILED DESCRIPTION

The following detailed description should be read with reference to the drawings, in which identical reference numbers refer to like elements throughout the different figures. The drawings, which are not necessarily to scale, depict selective examples and are not intended to limit the scope of inventive subject matter. The detailed description illustrates by way of example, not by way of limitation, the principles of inventive subject matter.

It is desirable to provide one or more compositions of matter, and methods for their use, that could be employed for treating human cancers by suppressing expression of one or more genes for human chorionic gonadotropin (hCG). In particular, it is desirable to provide one or more antisense phosphorodiamidate morpholino oligomers (hereinafter: MOs) that, upon introduction into one or more cells, suppress intracellular synthesis of the beta subunit of human chorionic gonadotropin (hCG-β).

Figure 1:
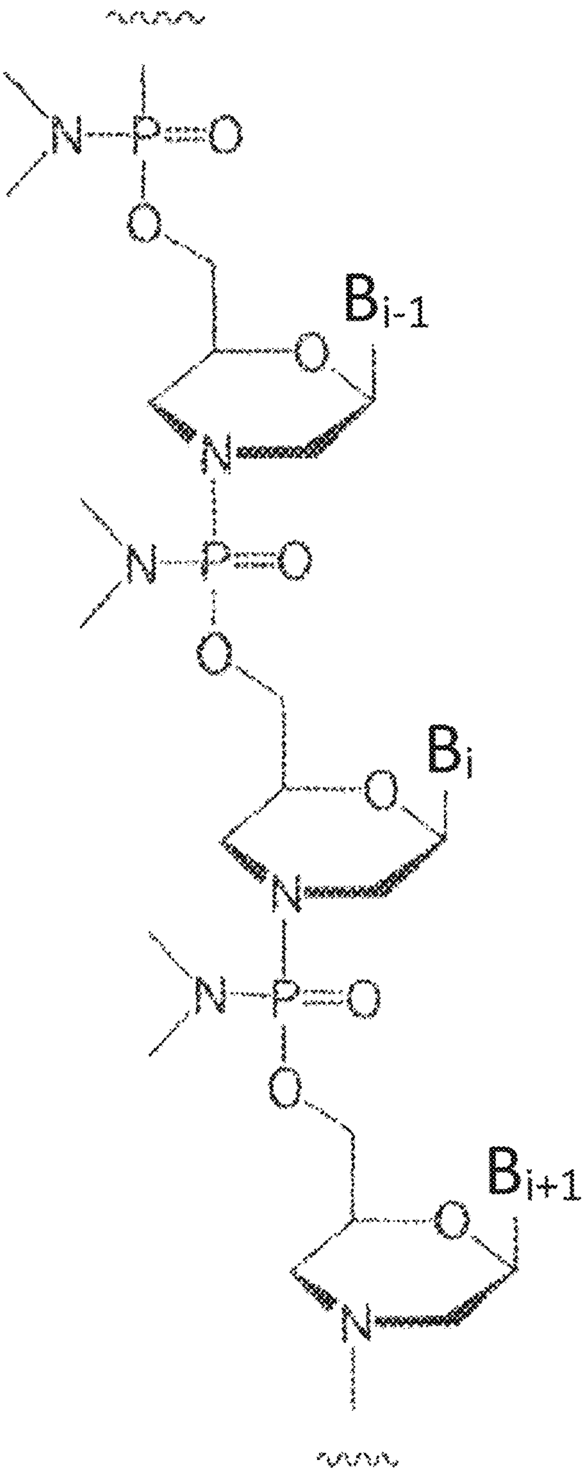
FIG. 1 shows the general structure of a portion of a phosphorodiamidate morpholino oligomer.

Antisense phosphorodiamidate morpholino oligomers (MOs) were developed in the late 1980s; see, e.g., U.S. Pat. No. 5,185,444 entitled "Uncharged morpholino-based polymers having phosphorous containing chiral intersubunit linkages" issued Feb. 9, 1993 to Summerton et al, which is incorporated herein by references in its entirety. The structure of MOs differs from that of more conventional nucleic-acid-based antisense oligonucleotides. Specifically, conventional antisense oligonucleotides typically contain 5-membered ribose or deoxyribose backbone ring structures joined by negatively charged inter-subunit linkages, with a corresponding base (adenine (A), cytosine (C), guanine (G), thymine (T), or uracil (U)) attached to the ring of each subunit. In contrast, MOs contain 6-membered morpholine backbone ring structures joined by non-ionic inter-subunit linkages, with a corresponding base (A, C, G, T, or U) attached to the ring of each subunit. Three subunits of a generic MO are shown in FIG. 1 and include corresponding bases $B_{i-1}$, $B_i$, and $B_{i+1}$.

The structural elements of MOs provide desirable properties in comparison to more conventional antisense agents. Specifically, MOs: (i) are generally resistant to degradation in biological systems (including in acidified lysosomes); (ii) provide high sequence specificity relative to other antisense structural types; (iii) do not require RNase H or RISC to function; (iv) are generally free of the non-antisense off-target effects exhibited by other antisense structural types; (v) provide predictable targeting of the selected RNA transcript; (vi) pass relatively freely between cytosol and nucleus of cells and function in both; (vii) have good aqueous solubility; (viii) are relatively more affordable due to inexpensive starting materials, efficient assembly, and easy workup; and are versatile in that they can (ix) alter splicing in the nucleus, (x) block protein translation in the cytosol, and (xi) block binding of regulatory proteins and non-coding RNAs throughout the cell.

An inventive composition of matter comprises an antisense phosphorodiamidate morpholino oligomer (MO) that includes an MO base sequence. The MO base sequence includes at least the base sequence gcagcccctggaacat (SEQ ID NO: 8) and is arranged to bind a corresponding complementary base sequence of messenger RNA (mRNA) transcribed from one or more genes for a beta subunit of human chorionic gonadotropin (hCG-β). In some examples, the one or more hCG-β genes can include one or more of the CGB3, CGB5, CGB7, or CGB8 genes; in some examples, the one or more hCG-β genes can include two or more of the CGB3, CGB5, CGB7, or CGB8 genes; in some examples, the one or more hCG-β genes can include all four of the CGB3, CGB5, CGB7, and CGB8 genes.

In some examples, the MO base sequence can comprise one of the first seven base sequences shown below, shown in the table of FIG. 2, and included in the appended sequence listing (MOTH02CP1_sequence_listing.xml). Each of those first seven base sequences includes at least the base sequence gcagcccctggaacat (SEQ ID NO: 8).

```
                                     SEQ ID NO: 1
gcagcagcccctggaacatctccatc

                                     SEQ ID NO: 2
cagcagcccctggaacatctccatc

                                     SEQ ID NO: 3
gcagcccctggaacatctccatcct

                                     SEQ ID NO: 4
cagcagcagcccctggaacatctcc

                                     SEQ ID NO: 5
gcaacagcagcagcccctggaacat

                                     SEQ ID NO: 6
cagcagcagcccctggaacatctccatc

                                     SEQ ID NO: 7
caacagcagcagcccctggaacatctcc

                                     SEQ ID NO: 8
gcagcccctggaacat
```

The non-ionic charge and large size of the MOs impedes their introduction into the intracellular space. A so-called "bare" MO (e.g., as in FIG. 3A) experiences only minimal cellular uptake. To enhance cellular uptake, in some examples one or more delivery moieties can be attached to the MO (covalently or otherwise); in some examples the MO can be contained by or incorporated into the delivery moiety. A typical delivery moiety can include one or more membrane-binding or membrane-penetrating species.

Figures 3A, 3B, 3C:
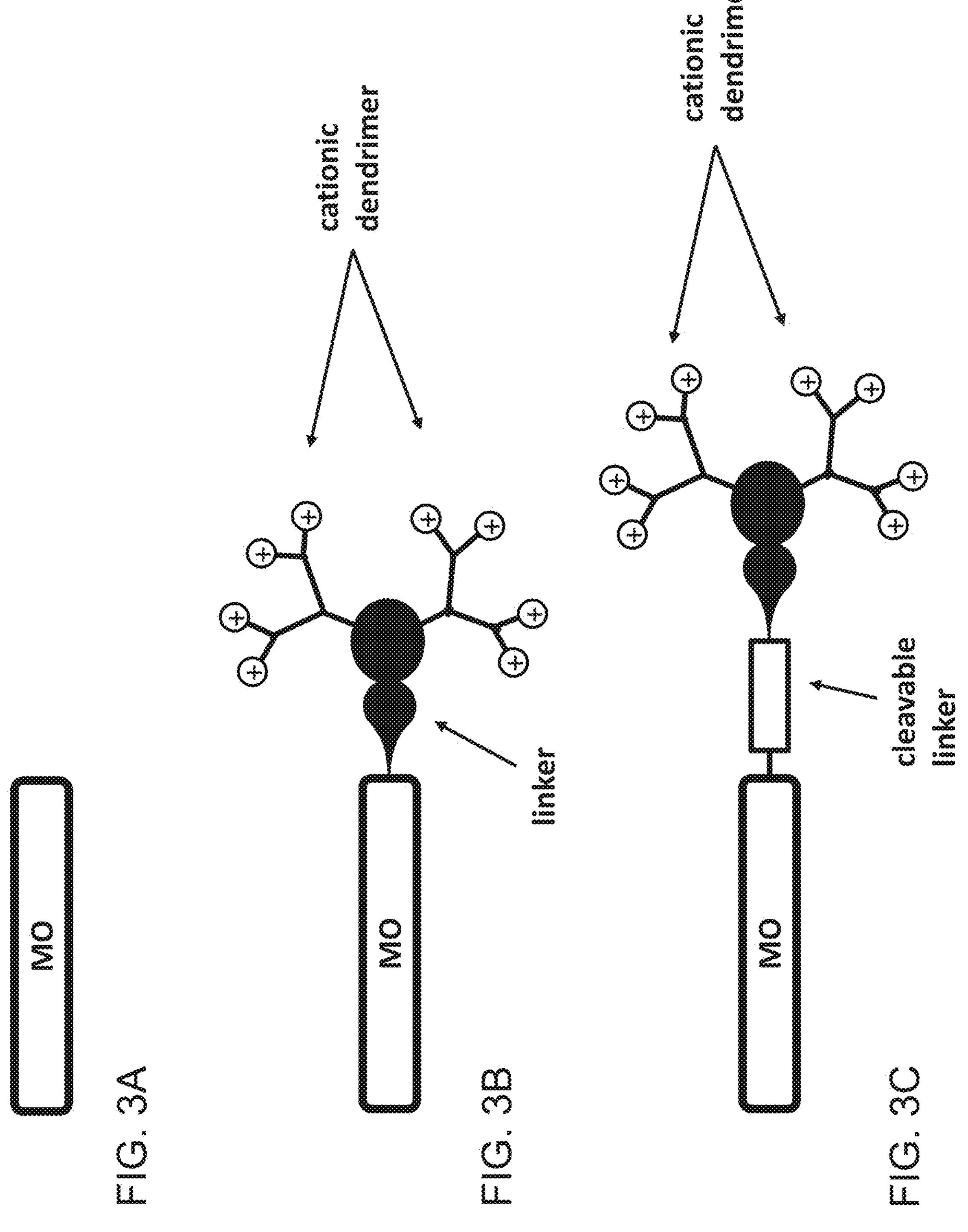
FIGS. 3A, 3B, and 3C are schematic representations of a so-called "bare" MO (FIG. 3A), an MO covalently linked to a cationic dendrimer (FIG. 3B), and an MO covalently linked to a cationic dendrimer by a cleavable linker (FIG. 3C).
Figure 4A:
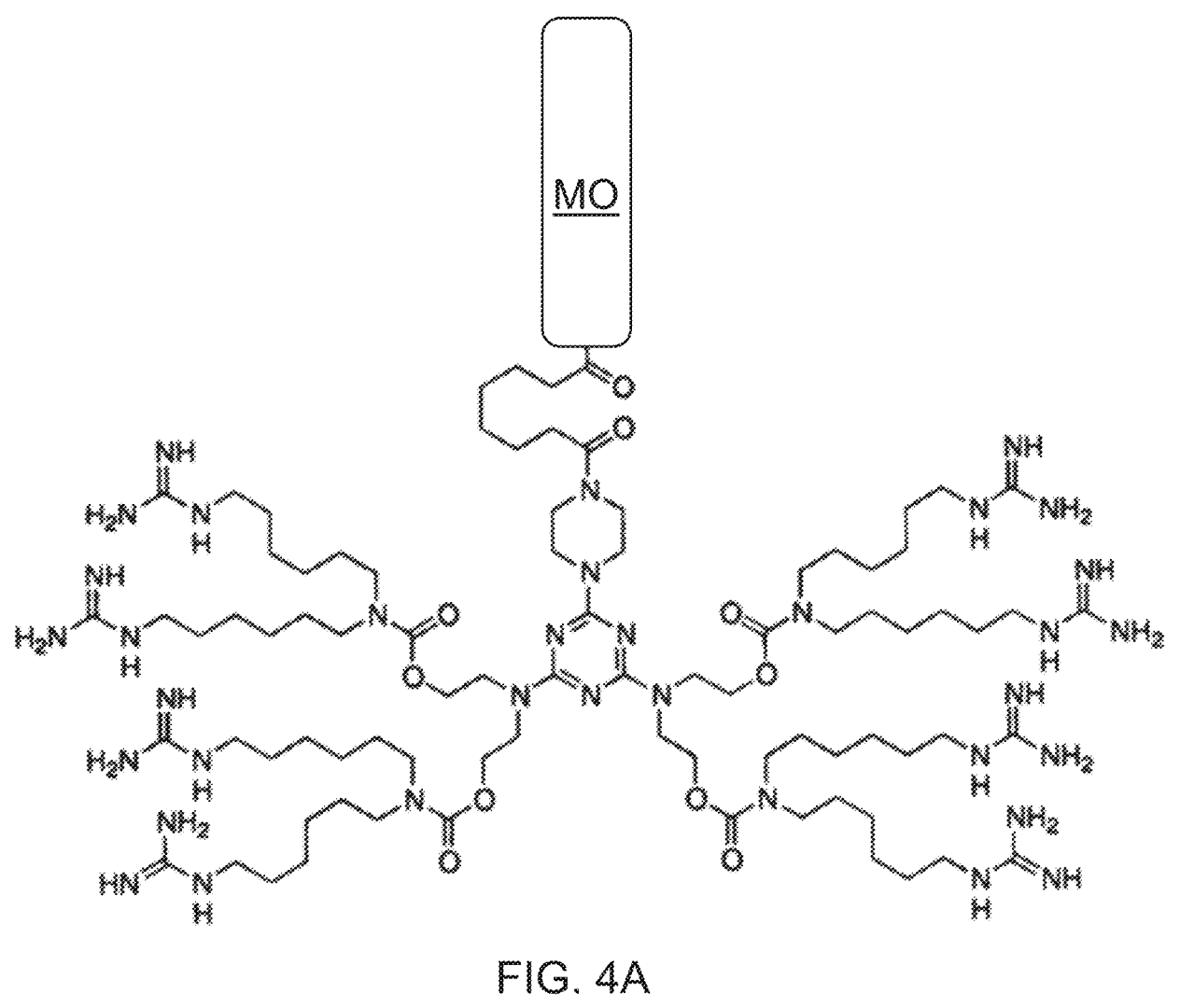
Figure 4B:
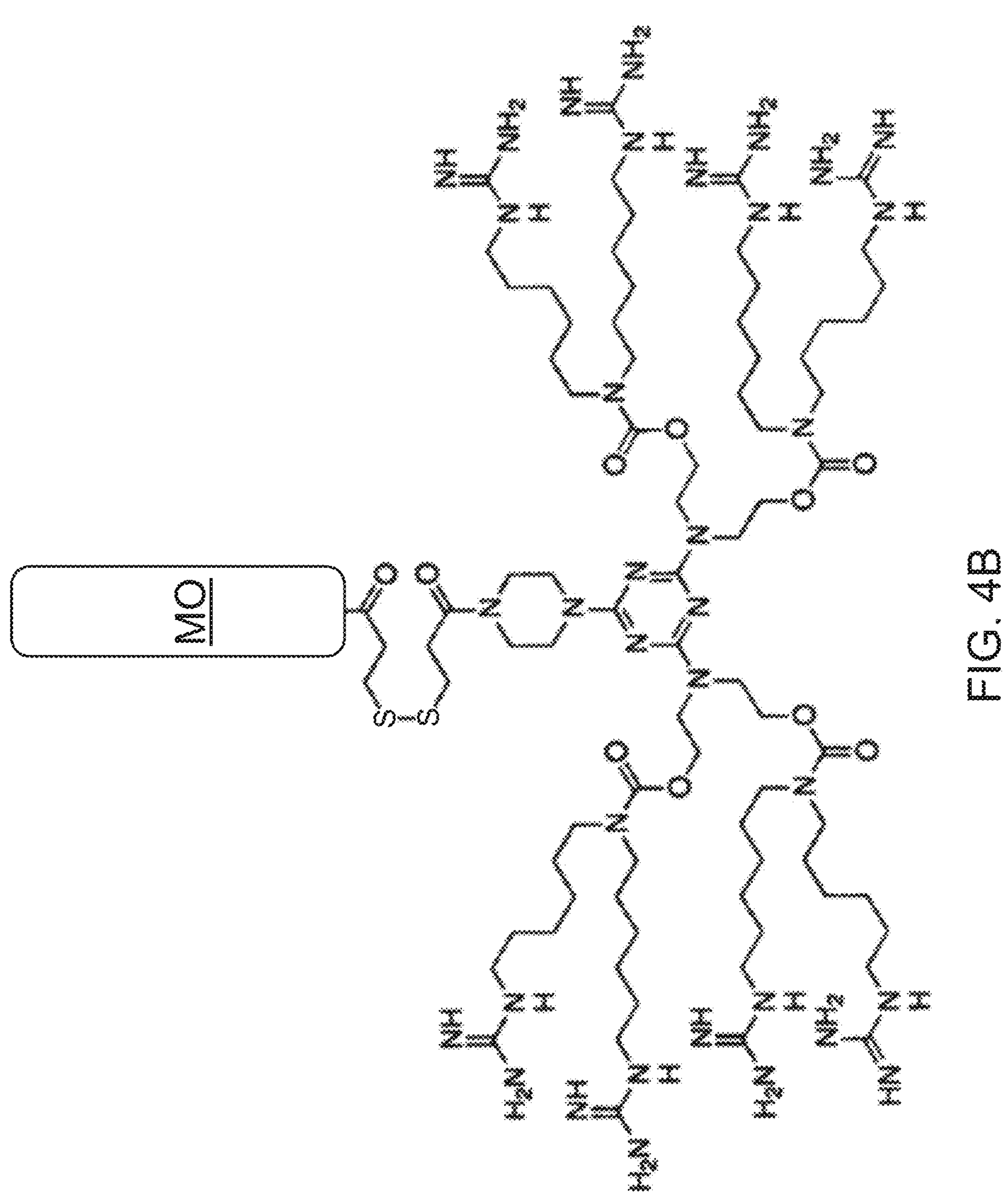
FIG. 4B shows the structure of a generic MO covalently linked (as in FIG. 3C, with a first specific example of a cleavable linker) to a specific example of a cationic dendrimer.

Some examples of such delivery moieties can include a cationic species, such as a cationic dendrimer (e.g., as in FIGS. 3B and 3C. The cationic dendrimer binds to the cell membrane and enables the MO to pass through the membrane into the cell. Some examples of suitable cationic delivery moieties are disclosed in, e.g., U.S. Pat. No. 7,935, 816 entitled "Molecular transporter compositions comprising dendrimeric oligoguanidine with a triazine core that facilitate delivery into cells in vivo" issued May 3, 2011 to Li, or US 2023/0357763 entitled "Morpholinos with increased delivery efficiency" published Nov. 9, 2023 in the names of Summerton et al; both of said patent and publication are incorporated herein by reference in their entireties. Corresponding examples are shown in FIG. 4A (from Li), FIG. 4B (from Li), and FIG. 4C (from Summerton). Each employs an octaguanidinium dendrimer in the delivery moiety (shown in its neutral state in the figures; under physiological conditions the guanidinium groups would be protonated and therefore positively charged). The octaguanidinium dendrimer is characterized by a nonlinear, non-peptidic, and non-natural architecture; other suitable dendrimers or classes of dendrimers, ionic or nonionic, can be employed. In some examples the cationic dendrimer can include at least 6 positive charges and not more than 12 positive charges. The cationic dendrimer enables efficient delivery of an MO into the cytosol of cells, greatly improving cellular uptake.

Figure 4C:
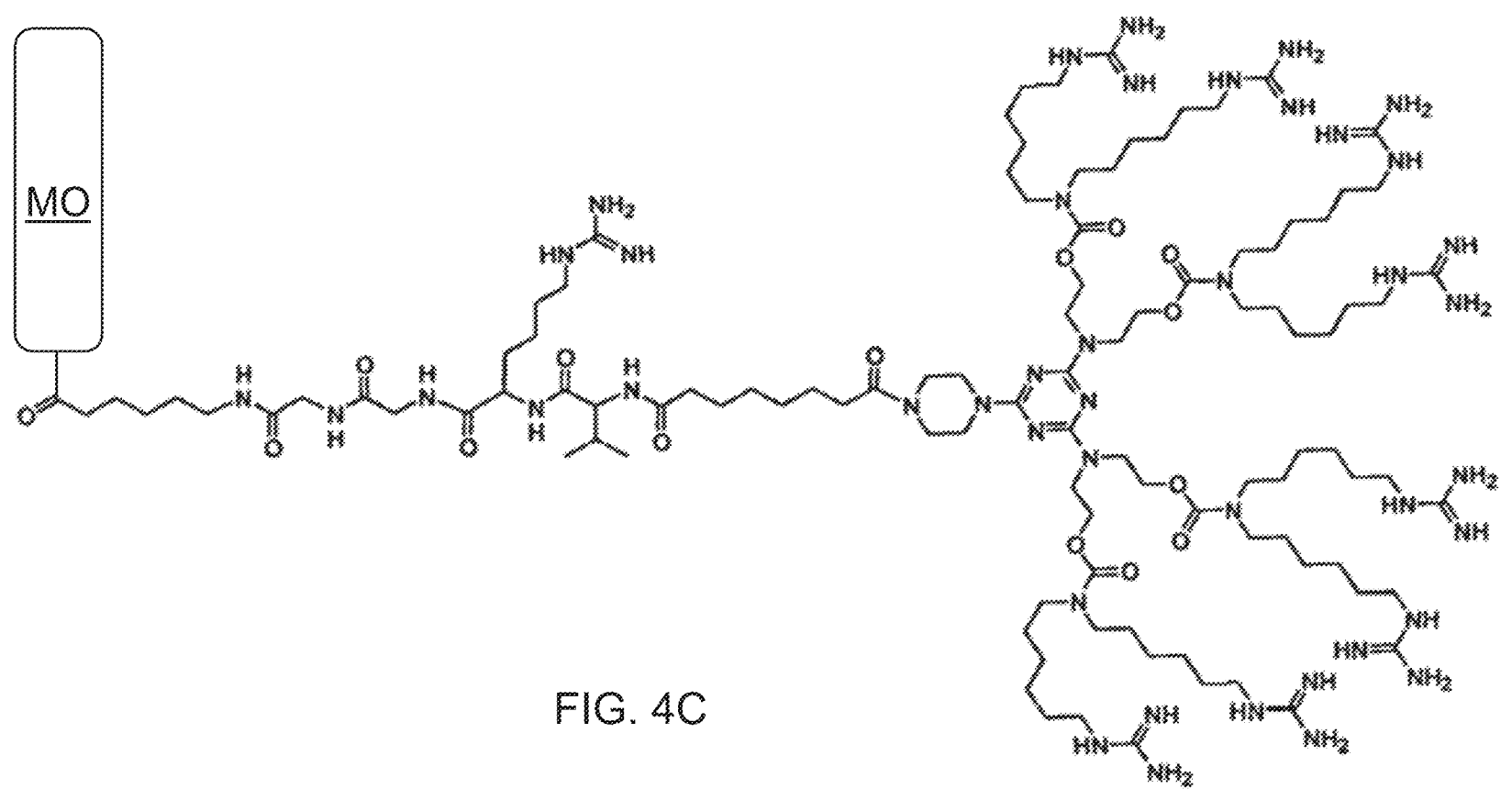

In some examples the delivery moiety can include a linker covalently bonded to the MO. For example, the cationic dendrimer or other suitable membrane-binding or membrane-penetrating species can be connected to the MO by the linker. In some examples the MO, linker, and dendrimer remain connected after entering the cell (e.g., as in FIG. 3B or 4A). In some other examples, cellular uptake can be further enhanced by arrangement of the linker to be cleaved in the intracellular environment (e.g., in the cytosol or in an acidified lysosome; e.g., as in FIG. 3C, 4B, or 4C). In some examples the linker can include a short peptide sequence of two or more amino acids (e.g., 4 or 8 amino acids, as in Summerton; FIG. 4C) that is cleaved after entering the cell. In some other examples the linker can include a disulfide bond (as in Li; FIG. 4B) or a carboxylic acid ester that is cleaved after entering the cell. Once separated from the cationic dendrimer (which tends to remain attached to the cell membrane), the MO can move freely about the intracellular space, including into the nucleus. That mobility increases the ability of the MO to bind the targeted sequences of mRNA to suppress synthesis of hCG-β within the cell.

Other suitable delivery moieties, including any suitable membrane-binding or membrane-penetrating species of any suitable type, or any suitable cleavable or non-cleavable linker of any suitable type, can be employed as needed or desired, including extant and future-developed moieties, species, or linkers. Examples can include but are not limited to: peptide moieties (including cell-penetrating peptides (CPPs) such as $(RXR)_4$, $(RXRRBR)_2XB$, DG9, D-chiral octarginine (r8), a so-called "phylomer" peptide (FPPa) such as PYC Tx, and so forth), lipid-based species (such as α-tocopherol or a long-chain fatty acid with a trans-4-hydroxyprolinol linker), receptor-ligand species (such as asialoglycoprotein receptor (ASGR) or N-acetylgalactosamine (GalNAc)), antibody or aptamer species (targeting, e.g., HIV gp160 protein, HER2, CD7, CD71, CD44, TMEFF2, EPHA2, EGFR, and so forth), polymer species (such as poly(glycerol), poly(2-oxazoline), poly(amino acid), poly[N-(2-hydroxypropyl) methacrylamide, and so forth), lipid nanoparticles or liposomes, or extracellular vesicles (e.g., exosomes, microvesicles, apoptotic bodies, and so forth).

Figure 5:
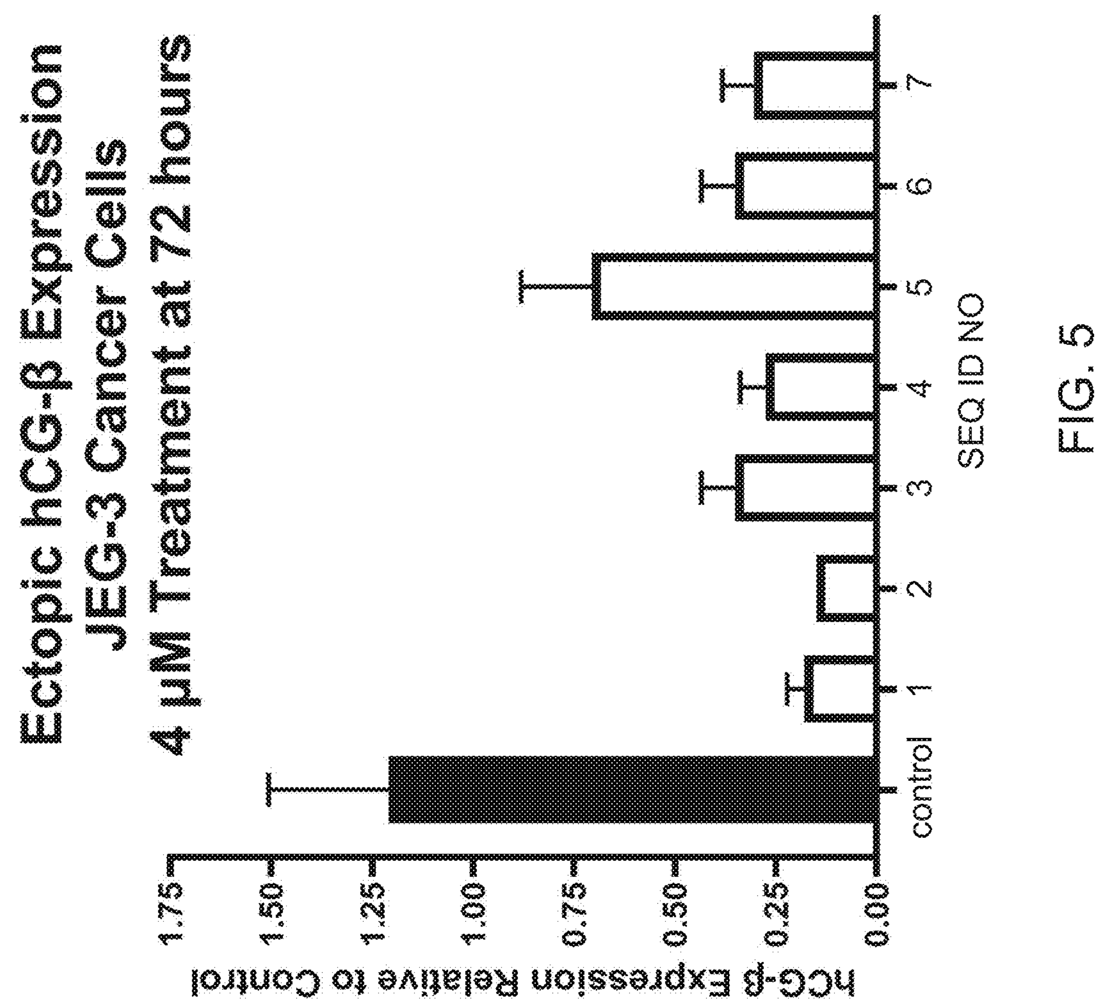
FIG. 5 is a plot of hCG-β expression in cultured cancer cells (JEG-3 cell line) treated with a control MO (no binding to hCG-β mRNA) versus those cultured cancer cells treated with an MO having one of the sequences listed in the table of FIG. 2.

To suppress intracellular synthesis of hCG-β, any of the MOs described above are introduced into one or more cells (e.g., cancer cells). The MO includes the MO base sequence that binds the corresponding complementary base sequence of messenger RNA (mRNA) transcribed from one or more genes for the beta subunit of human chorionic gonadotropin (hCG-β). That binding inactivates the mRNA and prevents synthesis of the hCG-β protein. In some examples intracellular synthesis of hCG-β can be reduced in the one or more cells by at least 50%, at least 60%, at least 70%, at least 80%, at least 90%, at least 95%, at least 99%, or 100%, relative to intracellular synthesis of hCG-β in the absence of any MO that binds the mRNA for hCG-β synthesis. Some experimental data reflecting that suppressed synthesis is shown in FIG. 5 for cultured cancer cells (JEG-3 cell line) treated with one of the seven MO base sequences of FIG. 2 (relative to a control MO that does not bind any portion of the mRNA for hCG-β synthesis).

Figure 6B:
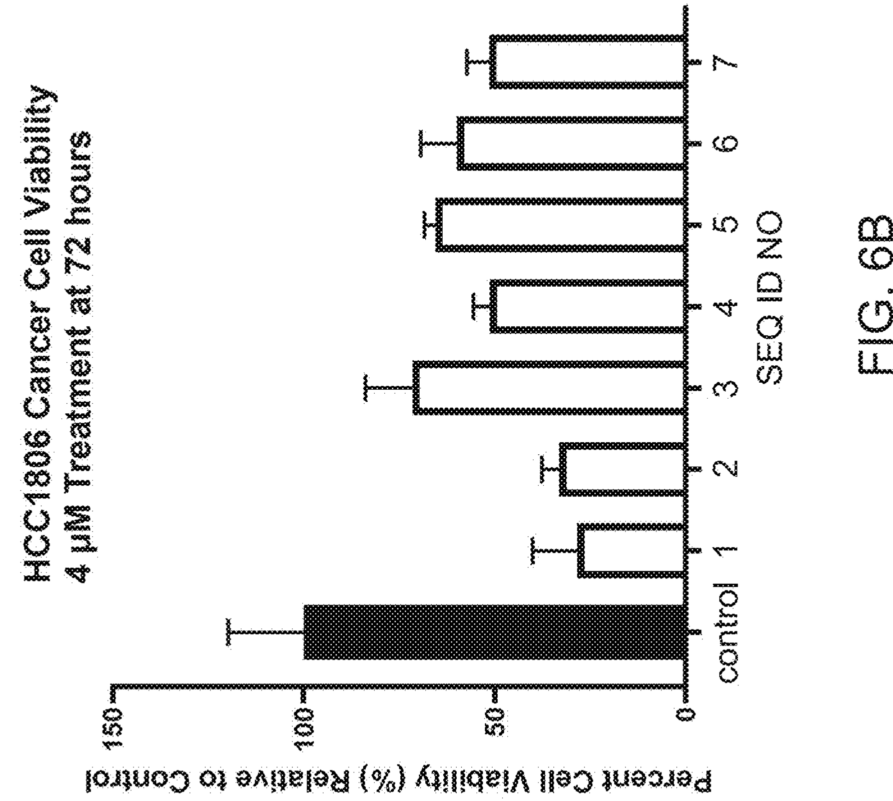
FIG. 6B is a plot of cell viability of cultured cancer cells (HCC1806 cell line) treated with a control MO (no binding to hCG-β mRNA) versus those cultured cells treated with an MO having one of the sequences listed in the table of FIG. 2.
Figure 6A:
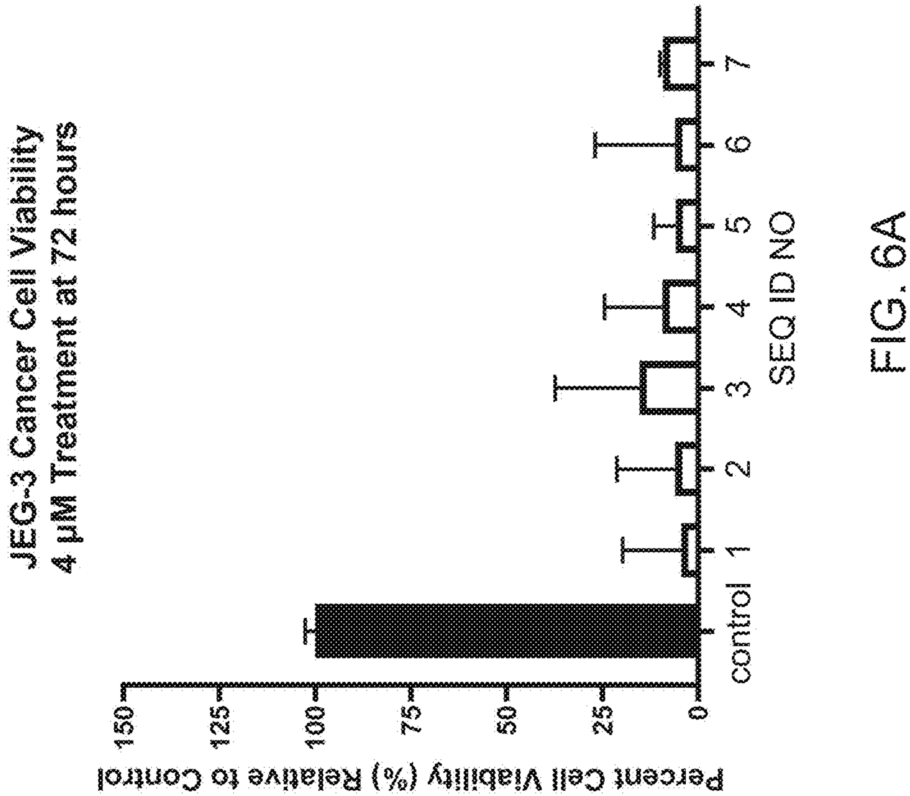
FIG. 6A is a plot of cell viability of cultured cancer cells (JEG-3 cell line) treated with a control MO (no binding to hCG-β mRNA) versus those cultured cells treated with an MO having one of the sequences listed in the table of FIG. 2.

In some examples the MO can be introduced into cancer cells using any suitable delivery technique or delivery medium. In some examples the MO can be introduced into the cancer cells in vitro, e.g., by adding a solution or suspension of the MO, including any delivery moiety (if present), into a culture medium or nutrient bath in which the cancer cells are grown; the MO can then be taken up by the cancer cells. In some other examples the MO can be introduced into the cancer cells in vivo, e.g., by administering a solution or suspension of the MO, including any delivery moiety (if present), to an organism or to a patient by intravenous infusion, intraperitoneal infusion, intratumoral injection, intramuscular injection, and so forth; upon reaching the cancer cells the MO can then be taken up by those cells. Because many (perhaps all) cancer cells are dependent on hCG-β, in some examples suppression of intracellular synthesis of hCG-β can result in death of at least 50%, at least 60%, at least 70%, at least 80%, at least 90%, at least 95%, at least 99%, or 100% of the cancer cells. Some experimental data reflecting that reduction of cell viability is shown in FIGS. 6A and 6B for cultured cancer cells (JEG-3 and HCC1806 cell lines, respectively) treated with one of the seven MO base sequences of FIG. 2 (relative to a control MO that does not bind any portion of the mRNA for hCG-β synthesis). In some examples suppressing intracellular synthesis of hCG-β in turn suppresses cell division of the cancer cells.

Examples of cancer cells exhibiting reduced intracellular synthesis of hCG-β, reduced viability, or reduced cell division can include but are not limited to: bladder cancer cells, cervical cancer cells, ovarian cancer cells, choriocarcinoma cancer cells, testicular cancer cells, brain cancer cells, glioblastoma cancer cells, leukemia cancer cells, acute monocytic leukemia cancer cells, pancreatic cancer cells, breast cancer cells, lung cancer cells, liver cancer cells, or colorectal cancer cells.

In addition to the preceding, the following example embodiments fall within the scope of the present disclosure or appended claims. Any given Example below that refers to multiple preceding Examples shall be understood to refer to only those preceding Examples with which the given Example is not inconsistent, and to exclude implicitly those preceding Examples with which the given Example is inconsistent.

Example 1. A composition of matter comprising an antisense phosphorodiamidate morpholino oligomer (MO) that includes an MO base sequence, the MO base sequence including at least the base sequence gcagcccctggaacat (SEQ ID NO: 8) and being arranged to bind a corresponding complementary base sequence of messenger RNA (mRNA) transcribed from one or more genes for a beta subunit of human chorionic gonadotropin (hCG-β).

Example 2. The composition of Example 1 wherein the one or more genes include one or more of CGB3, CGB5, CGB7, or CGB8.

Example 3. The composition of Example 1 wherein the one or more genes include two or more of CGB3, CGB5, CGB7, or CGB8.

Example 4. The composition of Example 1 wherein the one or more genes include CGB3, CGB5, CGB7, and CGB8.

Example 5. The composition of any one of Examples 1 through 4 wherein the MO base sequence is gcagcagcccctggaacatctccatc (SEQ IN NO: 1).

Example 6. The composition of any one of Examples 1 through 4 wherein the MO base sequence is cagcagcccctggaacatctccatc (SEQ ID NO: 2).

Example 7. The composition of any one of Examples 1 through 4 wherein the MO base sequence is one of (i) gcagcccctggaacatctccatcct (SEQ ID NO: 3), (ii) cagcagcagcccctggaacatctcc (SEQ ID NO: 4), (iii) gcaacagcagcagcccctggaacat (SEQ ID NO: 5), (iv) cagcagcagcccctggaacatctccatc (SEQ ID NO: 6), or (v) caacagcagcagcccctggaacatctcc (SEQ ID NO: 7).

Example 8. The composition of any one of Examples 1 through 7 further comprising a delivery moiety linked to, including, or containing the MO, the delivery moiety being structurally arranged for attaching to a membrane of a cell and enabling the MO to enter the cell.

Example 9. The composition of Example 8 wherein the delivery moiety comprises (i) a cationic dendrimer and (ii) a linker covalently bonded to the MO and to the cationic dendrimer so as to link the MO to the cationic dendrimer.

Example 10. The composition of Example 9 wherein the linker is arranged to be cleaved in an intracellular environment, cleavage of the linker resulting in separation of the MO from the cationic dendrimer.

Example 11. The composition of Example 9 wherein the cationic dendrimer is arranged so as to bind to a cell membrane and pass through the cell membrane along with the linker and the MO.

Example 12. The composition of any one of Examples 9 through 11 wherein the cationic dendrimer includes at least 6 positive charges and not more than 12 positive charges.

Example 13. The composition of any one of Examples 9 through 12 wherein the cationic dendrimer includes an octaguanidium dendrimer.

Example 14. The composition of Example 8 wherein the delivery moiety comprises (i) a membrane-binding or membrane-penetrating species and (ii) a linker covalently bonded to the MO and to the membrane-binding or membrane-penetrating species so as to link the MO to the membrane-binding or membrane-penetrating species.

Example 15. The composition of Example 14 wherein the linker includes a sequence of two or more amino acids.

Example 16. The composition of Example 14 wherein the linker includes a disulfide bond.

Example 17. The composition of any one of Examples 14 through 16 wherein the linker is arranged to be cleaved in an intracellular environment, cleavage of the linker resulting in separation of the MO from the membrane-binding or membrane-penetrating species.

Example 18. A method for suppressing intracellular synthesis of a beta subunit of human chorionic gonadotropin (hCG-β), the method comprising introducing into one or more cells the composition of any one of Examples 1 through 17.

Example 19. A method for suppressing intracellular synthesis of a beta subunit of human chorionic gonadotropin (hCG-β), the method comprising introducing into one or more cells an antisense phosphorodiamidate morpholino oligomer (MO) that includes an MO base sequence, the MO base sequence including at least the base sequence gcagcccctggaacat (SEQ ID NO: 8) and being arranged to bind a corresponding complementary base sequence of messenger RNA (mRNA) transcribed from one or more genes for the beta subunit of human chorionic gonadotropin (hCG-β).

Example 20. The method of Example 19 wherein the one or more genes include one or more of CGB3, CGB5, CGB7, or CGB8.

Example 21. The method of Example 19 wherein the one or more genes include two or more of CGB3, CGB5, CGB7, or CGB8.

Example 22. The method of Example 19 wherein the one or more genes include CGB3, CGB5, CGB7, and CGB8.

Example 23. The method any one of Examples 19 through 22 wherein the MO base sequence is gcagcagcccctggaacatctccatc (SEQ IN NO: 1).

Example 24. The method of any one of Examples 19 through 22 wherein the MO base sequence is cagcagcccctggaacatctccatc (SEQ ID NO: 2).

Example 25. The method of any one of Examples 19 through 22 wherein the MO base sequence is one of (i) gcagcccctggaacatctccatcct (SEQ ID NO: 3), (ii) cagcagcagcccctggaacatctcc (SEQ ID NO: 4), (iii) gcaacagcagcagcccctggaacat (SEQ ID NO: 5), (iv) cagcagcagcccctggaacatctccatc (SEQ ID NO: 6), or (v) caacagcagcagcccctggaacatctcc (SEQ ID NO: 7).

Example 26. The method of any one of Examples 19 through 25 wherein a delivery moiety is linked to, including, or containing the MO, the delivery moiety being structurally arranged for attaching to a membrane of a cell and enabling the MO to enter the cell.

Example 27. The method of Example 26 wherein the delivery moiety comprises (i) a cationic dendrimer and (ii) a linker covalently bonded to the MO and to the cationic dendrimer so as to link the MO to the cationic dendrimer.

Example 28. The method of Example 27 wherein the linker is arranged to be cleaved in an intracellular environment, cleavage of the linker resulting in separation of the MO from the cationic dendrimer.

Example 29. The method of Example 27 wherein the cationic dendrimer is arranged so as to bind to a cell membrane and pass through the cell membrane along with the linker and the MO.

Example 30. The method of any one of Examples 27 through 29 wherein the cationic dendrimer includes at least 6 positive charges and not more than 12 positive charges.

Example 31. The method of any one of Examples 27 through 30 wherein the cationic dendrimer includes an octaguanidium dendrimer.

Example 32. The method of Example 26 wherein the delivery moiety comprises (i) a membrane-binding or membrane-penetrating species and (ii) a linker covalently bonded to the MO and to the membrane-binding or membrane-penetrating species so as to link the MO to the membrane-binding or membrane-penetrating species.

Example 33. The method of Example 32 wherein the linker includes a sequence of two or more amino acids.

Example 34. The method of Example 32 wherein the linker includes a disulfide bond.

Example 35. The method of any one of Examples 32 through 34 wherein the linker is arranged to be cleaved in an intracellular environment, cleavage of the linker resulting in separation of the MO from the membrane-binding or membrane-penetrating species.

Example 36. The method of any one of Examples 18 through 35 wherein intracellular synthesis of hCG-β is reduced in the one or more cells by at least 50%, at least 60%, at least 70%, at least 80%, at least 90%, at least 95%, at least 99%, or 100%, relative to intracellular synthesis of hCG-β in the absence of the MO.

Example 37. The method of any one of Examples 18 through 36 wherein the one or more cells are cancer cells.

Example 38. The method of Example 37 wherein suppressing expression of the gene for hCG-β results in death of at least 50%, at least 60%, at least 70%, at least 80%, at least 90%, at least 95%, at least 99%, or 100% of the cancer cells.

Example 39. The method of any one of Examples 37 or 38 wherein suppressing intracellular synthesis of hCG-β in turn suppresses cell division of the cancer cells.

Example 40. The method of any one of Examples 37 through 39 wherein the MO is introduced into the cancer cells in vitro.

Example 41. The method of any one of Examples 37 through 39 wherein the MO is introduced into the cancer cells in vivo.

Example 42. The method of any one of Examples 37 through 41 wherein the cancer cells are bladder cancer cells, cervical cancer cells, ovarian cancer cells, choriocarcinoma cancer cells, testicular cancer cells, brain cancer cells, glioblastoma cancer cells, leukemia cancer cells, acute monocytic leukemia cancer cells, pancreatic cancer cells, breast cancer cells, lung cancer cells, liver cancer cells, or colorectal cancer cells.

This disclosure is illustrative and not limiting. Further modifications will be apparent to one skilled in the art in light of this disclosure and are intended to fall within the scope of the present disclosure or appended claims. It is intended that equivalents of the disclosed example embodiments and methods, or modifications thereof, shall fall within the scope of the present disclosure or appended claims.

In the foregoing Detailed Description, various features may be grouped together in several example embodiments for the purpose of streamlining the disclosure. This method of disclosure is not to be interpreted as reflecting an intention that any claimed embodiment requires more features than are expressly recited in the corresponding claim. Rather, as the appended claims reflect, inventive subject matter may lie in less than all features of a single disclosed example embodiment. Therefore, the present disclosure shall be construed as implicitly disclosing any embodiment having any suitable subset of one or more features—which features are shown, described, or claimed in the present application—including those subsets that may not be explicitly disclosed herein. A "suitable" subset of features includes only features that are neither incompatible nor mutually exclusive with respect to any other feature of that subset. Accordingly, the appended claims are hereby incorporated in their entirety into the Detailed Description, with each claim standing on its own as a separate disclosed embodiment. In addition, each of the appended dependent claims shall be interpreted, only for purposes of disclosure by said incorporation of the claims into the Detailed Description, as if written in multiple dependent form and dependent upon all preceding claims with which it is not inconsistent. It should be further noted that the cumulative scope of the appended claims can, but does not necessarily, encompass the whole of the subject matter disclosed in the present application.

The following interpretations shall apply for purposes of the present disclosure and appended claims. The words "comprising," "including," "having," and variants thereof, wherever they appear, shall be construed as open-ended terminology, with the same meaning as if a phrase such as "at least" were appended after each instance thereof, unless explicitly stated otherwise. The article "a" shall be interpreted as "one or more" unless "only one," "a single," or other similar limitation is stated explicitly or is implicit in the particular context; similarly, the article "the" shall be interpreted as "one or more of the" unless "only one of the," "a single one of the," or other similar limitation is stated explicitly or is implicit in the particular context. The conjunction "or" is to be construed inclusively unless: (i) it is explicitly stated otherwise, e.g., by use of "either . . . or," "only one of," or similar language; or (ii) two or more of the listed alternatives are understood or disclosed (implicitly or explicitly) to be incompatible or mutually exclusive within the particular context. In that latter case, "or" would be understood to encompass only those combinations involving non-mutually-exclusive alternatives. In one example, each of "a dog or a cat," "one or more of a dog or a cat," and "one or more dogs or cats" would be interpreted as one or more dogs without any cats, or one or more cats without any dogs, or one or more of each.

For purposes of the present disclosure or appended claims, when a numerical quantity is recited (with or without terms such as "about," "about equal to," "substantially equal to," "greater than about," "less than about," and so forth), standard conventions pertaining to measurement precision, rounding error, and significant digits shall apply, unless a differing interpretation is explicitly set forth, or if a differing interpretation is implicit or inherent (e.g., some small integer quantities). For null quantities described by phrases such as "equal to zero," "absent," "eliminated," "negligible," "prevented," and so forth (with or without terms such as "about," "substantially," and so forth), each such phrase shall denote the case wherein the quantity in question has been reduced or diminished to such an extent that, for practical purposes in the context of the intended operation or use of the disclosed or claimed apparatus or method, the overall behavior or performance of the apparatus or method does not differ from that which would have occurred had the null quantity in fact been completely removed, exactly equal to zero, or otherwise exactly nulled. Terms such as "parallel," "perpendicular," "orthogonal," "flush," "aligned," and so forth shall be similarly interpreted (with or without terms such as "about," "substantially," and so forth).

For purposes of the present disclosure and appended claims, any labelling of elements, steps, limitations, or other portions of an embodiment, example, or claim (e.g., first, second, third, etc., (a), (b), (c), etc., or (i), (ii), (iii), etc.) is only for purposes of clarity, and shall not be construed as implying any sort of ordering or precedence of the portions so labelled. If any such ordering or precedence is intended, it will be explicitly recited in the embodiment, example, or claim or, in some instances, it will be implicit or inherent based on the specific content of the embodiment, example, or claim. In the appended claims, if the provisions of 35 USC § 112(f) are desired to be invoked in an apparatus claim, then the word "means" will appear in that apparatus claim. If those provisions are desired to be invoked in a method claim, the words "a step for" will appear in that method claim. Conversely, if the words "means" or "a step for" do not appear in a claim, then the provisions of 35 USC § 112(f) are not intended to be invoked for that claim.

If any one or more disclosures are incorporated herein by reference and such incorporated disclosures conflict in part or whole with, or differ in scope from, the present disclosure, then to the extent of conflict, broader disclosure, or broader definition of terms, the present disclosure controls. If such incorporated disclosures conflict in part or whole with one another, then to the extent of conflict, the later-dated disclosure controls.

The Abstract is provided as required as an aid to those searching for specific subject matter within the patent literature. However, the Abstract is not intended to imply that any elements, features, or limitations recited therein are necessarily encompassed by any particular claim. The scope of subject matter encompassed by each claim shall be determined by the recitation of only that claim.

What is claimed is:

1. A composition of matter comprising an antisense phosphorodiamidate morpholino oligomer (MO) that includes an MO base sequence, the MO base sequence including at least the base sequence gcagcccctggaacat (SEQ ID NO: 8) and being arranged to bind a corresponding complementary base sequence of messenger RNA (mRNA) transcribed from one or more genes for a beta subunit of human chorionic gonadotropin (hCG-β).

2. The composition of claim 1 wherein the one or more genes include one or more of CGB3, CGB5, CGB7, or CGB8.

3. The composition of claim 1 wherein the MO base sequence is cagcagcccctggaacatctccato (SEQ ID NO: 2).

4. The composition of claim 1 wherein the MO base sequence is one of:

(i) gcagcccctggaacatctccatcct (SEQ ID NO: 3), (ii) cagcagcagcccctggaacatctcc (SEQ ID NO: 4), (iii) gcaacagcagcagcccctggaacat (SEQ ID NO: 5), (iv) cagcagcagcccctggaacatctccato (SEQ ID NO: 6), or (v) caacagcagcagcccctggaacatctcc (SEQ ID NO: 7).

5. The composition of claim 1 further comprising a delivery moiety linked to, including, or containing the MO, the delivery moiety being structurally arranged for attaching to a membrane of a cell and enabling the MO to enter the cell.

6. The composition of claim 5 wherein the delivery moiety comprises (i) a membrane-binding or membrane-penetrating species and (ii) a linker covalently bonded to the MO and to the membrane-binding or membrane-penetrating species so as to link the MO to the membrane-binding or membrane-penetrating species.

7. The composition of claim 6 wherein the linker is arranged to be cleaved in an intracellular environment, cleavage of the linker resulting in separation of the MO from the membrane-binding or membrane-penetrating species.

8. A method for suppressing intracellular synthesis of a beta subunit of human chorionic gonadotropin (hCG-β), the method comprising introducing into one or more cells an antisense phosphorodiamidate morpholino oligomer (MO) that includes an MO base sequence, the MO base sequence including at least the base sequence gcagcccctggaacat (SEQ ID NO: 8) and being arranged to bind a corresponding complementary base sequence of messenger RNA (mRNA) transcribed from one or more genes for the beta subunit of human chorionic gonadotropin (hCG-β).

9. The method of claim 8 wherein the one or more genes include one or more of CGB3, CGB5, CGB7, or CGB8.

10. The method of claim 8 wherein the MO base sequence is cagcagcccctggaacatctccatc (SEQ ID NO: 2).

11. The method of claim 8 wherein the MO base sequence is one of:

(i) gcagcccctggaacatctccatcct (SEQ ID NO: 3), (ii) cagcagcagcccctggaacatctcc (SEQ ID NO: 4), (iii) gcaacagcagcagcccctggaacat (SEQ ID NO: 5), (iv) cagcagcagcccctggaacatctccatc (SEQ ID NO: 6), or (v) caacagcagcagcccctggaacatctcc (SEQ ID NO: 7).

12. The method of claim 8 wherein a delivery moiety includes, contains, or is linked to the MO, the delivery moiety being structurally arranged for attaching to a membrane of a cell and enabling the MO to enter the cell.

13. The method of claim 12 wherein the delivery moiety comprises (i) a membrane-binding or membrane-penetrating species and (ii) a linker covalently bonded to the MO and to the membrane-binding or membrane-penetrating species so as to link the MO to the membrane-binding or membrane-penetrating species.

14. The method of claim 13 wherein the linker is arranged to be cleaved in an intracellular environment, cleavage of the linker resulting in separation of the MO from the membrane-binding or membrane-penetrating species.

15. The method of claim 8 wherein intracellular synthesis of hCG-β is reduced in the one or more cells by at least 50% relative to intracellular synthesis of hCG-β in the absence of the MO.

16. The method of claim 8 wherein the one or more cells are cancer cells.

17. The method of claim 16 wherein suppressing expression of the gene for hCG-β results in death of at least 50% of the cancer cells.

18. The method of claim 16 wherein suppressing intracellular synthesis of hCG-β in turn suppresses cell division of the cancer cells.

19. The method of claim 16 wherein the MO is introduced into the cancer cells in vitro.

20. The method of claim 16 wherein the MO is introduced into the cancer cells in vivo.

* * * * *

SEQUENCE LISTING

```
Sequence total quantity: 8
SEQ ID NO: 1            moltype = DNA  length = 26
FEATURE                 Location/Qualifiers
source                  1..26
                        mol_type = other DNA
                        organism = synthetic construct
unsure                  1..26
                        note = antisense phosphorodiamidate morpholino oligomer
SEQUENCE: 1
gcagcagccc ctggaacatc tccatc                                          26

SEQ ID NO: 2            moltype = DNA  length = 25
FEATURE                 Location/Qualifiers
source                  1..25
                        mol_type = other DNA
                        organism = synthetic construct
unsure                  1..25
                        note = antisense phosphorodiamidate morpholino oligomer
SEQUENCE: 2
cagcagcccc tggaacatct ccatc                                           25

SEQ ID NO: 3            moltype = DNA  length = 25
FEATURE                 Location/Qualifiers
source                  1..25
                        mol_type = other DNA
                        organism = synthetic construct
unsure                  1..25
                        note = antisense phosphorodiamidate morpholino oligomer
SEQUENCE: 3
gcagcccctg gaacatctcc atcct                                           25

SEQ ID NO: 4            moltype = DNA  length = 25
FEATURE                 Location/Qualifiers
source                  1..25
                        mol_type = other DNA
                        organism = synthetic construct
unsure                  1..25
                        note = antisense phosphorodiamidate morpholino oligomer
SEQUENCE: 4
cagcagcagc ccctggaaca tctcc                                           25

SEQ ID NO: 5            moltype = DNA  length = 25
FEATURE                 Location/Qualifiers
source                  1..25
                        mol_type = other DNA
                        organism = synthetic construct
unsure                  1..25
                        note = antisense phosphorodiamidate morpholino oligomer
SEQUENCE: 5
gcaacagcag cagcccctgg aacat                                           25

SEQ ID NO: 6            moltype = DNA  length = 28
FEATURE                 Location/Qualifiers
source                  1..28
                        mol_type = other DNA
                        organism = synthetic construct
unsure                  1..28
                        note = antisense phosphorodiamidate morpholino oligomer
SEQUENCE: 6
cagcagcagc ccctggaaca tctccatc                                        28

SEQ ID NO: 7            moltype = DNA  length = 28
FEATURE                 Location/Qualifiers
source                  1..28
                        mol_type = other DNA
                        organism = synthetic construct
unsure                  1..28
                        note = antisense phosphorodiamidate morpholino oligomer
SEQUENCE: 7
caacagcagc agcccctgga acatctcc                                        28
```

-continued

```
SEQ ID NO: 8            moltype = DNA  length = 16
FEATURE                 Location/Qualifiers
source                  1..16
                        mol_type = other DNA
                        organism = synthetic construct
unsure                  1..16
                        note = antisense phosphorodiamidate morpholino oligomer
SEQUENCE: 8
gcagcccctg gaacat                                                  16
```